United States Patent
Sabbagh et al.

(10) Patent No.: US 10,821,107 B2
(45) Date of Patent: *Nov. 3, 2020

(54) INHIBITORS OF THE FKBP51 PROTEIN FROM A HIGH-THROUGHPUT DRUG SCREEN AND METHODS OF USE

(71) Applicant: UNIVERSITY OF SOUTH FLORIDA, Tampa, FL (US)

(72) Inventors: Jonathan Jacob Sabbagh, Tampa, FL (US); Chad Dickey, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/949,703

(22) Filed: Apr. 10, 2018

(65) Prior Publication Data

US 2018/0296554 A1    Oct. 18, 2018

Related U.S. Application Data

(63) Continuation of application No. 15/209,594, filed on Jul. 13, 2016, now Pat. No. 9,962,379, which is a continuation of application No. 14/788,364, filed on Jun. 30, 2015, now Pat. No. 9,399,039.

(51) Int. Cl.
| | |
|---|---|
| *A61K 31/496* | (2006.01) |
| *A61K 31/5415* | (2006.01) |
| *A61K 31/4168* | (2006.01) |
| *A61K 31/454* | (2006.01) |
| *A61K 45/06* | (2006.01) |
| *A61K 31/135* | (2006.01) |
| *A61K 31/137* | (2006.01) |
| *A61K 31/15* | (2006.01) |
| *A61K 31/42* | (2006.01) |
| *A61K 31/46* | (2006.01) |
| *A61K 31/138* | (2006.01) |
| *A61K 31/36* | (2006.01) |
| *C12Q 1/533* | (2006.01) |

(52) U.S. Cl.
CPC .......... *A61K 31/496* (2013.01); *A61K 31/135* (2013.01); *A61K 31/137* (2013.01); *A61K 31/138* (2013.01); *A61K 31/15* (2013.01); *A61K 31/36* (2013.01); *A61K 31/4168* (2013.01); *A61K 31/42* (2013.01); *A61K 31/454* (2013.01); *A61K 31/46* (2013.01); *A61K 31/5415* (2013.01); *A61K 45/06* (2013.01); *C12Q 1/533* (2013.01); *G01N 2333/99* (2013.01)

(58) Field of Classification Search
None
See application file for complete search history.

(56) References Cited

U.S. PATENT DOCUMENTS

| | | | |
|---|---|---|---|
| 4,938,949 | A | 7/1990 | Borch et al. |
| 2007/0298027 | A1 | 12/2007 | Binder et al. |

FOREIGN PATENT DOCUMENTS

| | | |
|---|---|---|
| EP | 2589383 | 5/2013 |
| WO | WO 2005/054500 | 6/2005 |
| WO | WO 2013/091900 | 6/2013 |
| WO | WO 2014/015993 | 1/2014 |
| WO | WO 2015/039758 | 3/2015 |
| WO | WO 2015/110271 | 7/2015 |

OTHER PUBLICATIONS

Kumar, Salt Selection in Drug Development. Pharmaceutical Technology. 32(3), Mar. 2, 2008, pp. 1-11.*
O'Leary, J. et al. "FKBP5 gene deletion prevents susceptibility to depression," Society for Neuroscience, Presented at 41$^{st}$ Annual Meeting of the Society for Neuroscience, Washington, D.C., Nov. 16, 2011, vol. 41, pp. 1-2, Abstract.
Strang, R.R. "Experiences With Cogentin in the Treatment of Parkinsonism," *Acta. Neurol. Scandinav.*, 1965, pp. 413-418, vol. 41, No. 4.
Tislow, R.F. "Usefulness of Anticholinergic Drugs in Suppressing Symptoms of Depression in Man," *Federation Proceedings, Federation of American Societies for Experimental Biology*, Jan. 1, 1969, p. 728, vol. 28, No. 2. Abtract.
Cao, W. et al., "FKBP immunophilins and Alzheimer's disease: A chaperoned affair," *J. Biosci.*, 2011, vol. 36, No. 3, pp. 493-498.
Ellsworth, K. et al., "FKBP5 genetic variation: association with selective serotonin reuptake inhibitor treatment outcomes in major depressive disorder," *Pharmaco. Genomics*, 2013, vol. 23, No. 3, pp. 156-166.
Sinars, C. et al., "Structure of the large FK506-binding protein FKBP51, an Hsp90-binding protein and a component of steroid receptor complexes," *PNAS*, 2003, vol. 100, No. 3, pp. 868-873.
Stechschulte, L. et al., "FKBP51 Reciprocally Regulates GRα and PPARγ Activation via the Akt-p38 Pathway," *Mol. Endocrinol.*, 2014, vol. 28, No. 8, pp. 1254-1264.

(Continued)

*Primary Examiner* — Samantha L Shterengarts
(74) *Attorney, Agent, or Firm* — Quarles & Brady LLP

(57) ABSTRACT

The subject invention concerns materials and methods for treating depression, stress disorders, such as PTSD, anxiety disorders, and/or a neurodegenerative disease or condition in a person or animal. In one embodiment, a person or animal in need of treatment is administered one or more compounds or drugs, or a composition comprising the one or more compounds or drugs, that inhibit FKBP51 activity or function. The subject invention also concerns a method for inhibiting activity of the FKBP51 protein in a cell. The subject invention also concerns methods of screening for compounds or drugs that inhibit the FKBP51 protein.

16 Claims, No Drawings

(56) References Cited

OTHER PUBLICATIONS

Storer, C. et al., "FKBP51 and FKBP52 in signaling and disease," *Trends in Endocrinology and Metabolism,* 2011, vol. 22, No. 12, pp. 481-490.

\* cited by examiner

INHIBITORS OF THE FKBP51 PROTEIN FROM A HIGH-THROUGHPUT DRUG SCREEN AND METHODS OF USE

CROSS-REFERENCE TO RELATED APPLICATIONS

The present application is a continuation of U.S. application Ser. No. 15/209,594, filed Jul. 13, 2016, which is a continuation of U.S. application Ser. No. 14/788,364, filed Jun. 30, 2015, which is hereby incorporated by reference herein in its entirety, including any figures, tables, nucleic acid sequences, amino acid sequences, or drawings.

BACKGROUND OF THE INVENTION

The FK506 binding protein 51 kDa (FKBP51) (Sinars et al., 2003) (Genbank Accession Nos. AAC51189.1 and AAC86983.1) is an important co-chaperone of the heat shock protein 90 kDa (Hsp90) machinery. Single nucleotide polymorphisms (SNPs) in FKBP5, the gene coding for FKBP51, can lead to elevated levels of FKBP51 and susceptibility to major depression, post-traumatic stress disorder (PTSD), and anxiety disorders. Furthermore, FKBP51 levels increase with age and are further elevated in the brains of Alzheimer's disease (AD) patients. These findings have called attention to FKBP51, with growing efforts being directed at discovering potential therapeutic compounds to inhibit the protein. Unfortunately there are no current treatments available that target this protein. FKBP51 exhibits functional control of stress hormone receptors, most notably the glucocorticoid receptor (GR), decreasing affinity of glucocorticoids for the receptor and preventing its nuclear translocation (Stechschulte et al., 2014).

BRIEF SUMMARY OF THE INVENTION

The subject invention concerns materials and methods for treating depression, stress disorders, such as PTSD, anxiety disorders, and/or a neurodegenerative disease or condition in a person or animal. In one embodiment, a person or animal in need of treatment is administered one or more compounds or drugs, or a composition comprising the one or more compounds or drugs, that inhibit FKBP51 activity or function. In one embodiment, the compound or drug is benztropine, clonidine, pimozide, thioridazine, trifluoperazine, or triflupromazine. The subject invention also concerns a method for inhibiting activity of the FKBP51 protein in a cell. The subject invention also concerns methods of screening for compounds or drugs that inhibit the FKBP51 protein.

DETAILED DESCRIPTION OF THE INVENTION

The subject invention concerns materials and methods for treating depression, stress disorders, such as PTSD, anxiety disorders, and/or a neurodegenerative disease or condition in a person or animal. In one embodiment, a person or animal in need of treatment is administered one or more compounds or drugs, or a composition comprising the one or more compounds or drugs, that inhibit FKBP51 activity or function. In a specific embodiment, the compound or drug is one that lessens or attenuates the suppressive effects of FKBP51 on glucocorticoid receptor (GR) activity. In one embodiment, the compound or drug is provided in the form of a pharmaceutically acceptable salt. In a more specific embodiment, the compound or drug is benztropine (e.g., benz- tropine mesylate), clonidine (e.g., clonidine hydrochloride), pimozide, thioridazine (e.g., thioridazine hydrochloride), trifluoperazine (e.g., trifluoperazine dihydrochloride), or triflupromazine (e.g., triflupromazine hydrochloride). A composition comprising the compound or drug can also comprise a pharmaceutically and/or physiologically acceptable carrier, buffer, or diluent.

In one embodiment of the method, the person or animal exhibits elevated levels of FKBP51 relative to pre-established control levels or to levels of a healthy or normal person or animal. In another embodiment, the person or animal has Alzheimer's disease or a disease similar to Alzheimer's disease. In a further embodiment, the person or animal exhibits one or more SNPs in the FKBP5 gene that are associated with elevated levels of FKBP51 protein relative to persons or animals that lack such SNPs. SNPs associated with elevated levels of FKBP51 protein are known in the art. In one embodiment, a method of the invention further comprises a step of determining whether the person or animal exhibits elevated levels of FKBP51 relative to a control and/or exhibits one or more SNPs that are associated with elevated levels of FKBP51.

The subject invention also concerns a method for inhibiting activity of the FKBP51 protein in a cell. In one embodiment, a cell is contacted with an effective amount of a compound or drug, or a composition comprising the compound or drug, that inhibits activity or function of a FKBP51 protein. In one embodiment, the cell exhibits an increased level of FKBP51 protein in the cell relative to a control cell. In a specific embodiment, the compound or drug is one that attenuates the suppressive effects of FKBP51 on glucocorticoid receptor (GR) activity. In a more specific embodiment, the compound or drug is benztropine (e.g., benztropine mesylate), clonidine (e.g., clonidine hydrochloride), pimozide, thioridazine (e.g., thioridazine hydrochloride), trifluoperazine (e.g., trifluoperazine dihydrochloride), or triflupromazine (e.g., triflupromazine hydrochloride). In one embodiment, the cell is a mammalian cell. In a specific embodiment, the cell is a human cell. In one embodiment, the cell is a neural cell. In another embodiment, the cell is a non-neural cell. The cell can be present in an in vitro or an in vivo environment.

The subject invention also concerns methods of screening for compounds or drugs that inhibit the FKBP51 protein. In one embodiment, a cell is contacted with a compound or drug to be screened, followed by determining if the compound or drug inhibited the activity or function of FKBP51 in the cell. In a specific embodiment, the compound or drug is screened for its ability to attenuate the suppressive effects of FKBP51 on GR activity. In one embodiment, the cell is a mammalian cell. In a specific embodiment, the cell is a human cell. In one embodiment, the cell is a neural cell. In another embodiment, the cell is a non-neural cell.

The subject invention also concerns compositions comprising one or more drugs or compounds of the invention. In one embodiment, the drug or compound is benztropine (e.g., benztropine mesylate), clonidine (e.g., clonidine hydrochloride), pimozide, thioridazine (e.g., thioridazine hydrochloride), trifluoperazine (e.g., trifluoperazine dihydrochloride), or triflupromazine (e.g., triflupromazine hydrochloride). In a further embodiment, a composition of the invention comprises one or more drugs or compounds of the invention and one or more drugs or compounds approved for treating depression, a stress or anxiety disorder, or a neurodegenerative disease or condition. In one embodiment, a composition of the invention further comprises one or more of donepezil, galantamine, vivastigmine, memantine, rivastigmine, or selegiline. In another embodiment, a composition further comprises one or more of monoamine oxidase (MAO) inhibitors such as phenelzine, tranylcypromine, isocarboxazid, and selegiline; antiepileptic drugs; selective serotonin reuptake inhibitors (SSRI), such as citalopram, escitalopram, fluvoxamine, fluoxetine, vortioxetine, paroxetine, sertraline, rasagiline, selegiline, L-dopa, carbidopa, and benserazide, or an isomer or analog thereof serotonin-norepinephrine reuptake inhibitors (SNRI), such as venlafaxine, desvenlafaxine, duloxetine, levomilnacipran, sibutramine, and milnacipran; tricyclic antidepressants (TCAs), such as amitriptyline, desipramine, doxepin, imipramine, nortriptyline, protriptyline, and trimipramine; 3,4-methylenedioxy-N-methylamphetamine (MDMA); propranolol; and ziprasidone, and risperidone, prazosin, mirtazapine, venlafaxine, lithium, bupropion, trazodone, and carbamazepine, or an isomer or analog thereof.

The subject invention also concerns kits comprising in one or more containers: a drug or compound of the invention or a composition comprising the drug or compound, or a pharmaceutically or physiologically acceptable salt and/or analog thereof, and optionally one or more compounds used to treat or prevent a neurodegenerative condition or depression, or an anxiety or stress disorder. In one embodiment, a kit of the invention comprises one or more of benztropine (e.g., benztropine mesylate), clonidine (e.g., clonidine hydrochloride), pimozide, thioridazine (e.g., thioridazine hydrochloride), trifluoperazine (e.g., trifluoperazine dihydrochloride), or triflupromazine (e.g., triflupromazine hydrochloride). In one embodiment, a kit of the invention further comprises one or more of donepezil, galantamine, vivastigmine, memantine, rivastigmine, or selegiline. In another embodiment, a kit further comprises one or more of monoamine oxidase (MAO) inhibitors such as phenelzine, tranylcypromine, isocarboxazid, and selegiline; antiepileptic drugs; selective serotonin reuptake inhibitors (SSRI), such as citalopram, escitalopram, fluvoxamine, fluoxetine, vortioxetine, paroxetine, sertraline, rasagiline, selegiline, L-dopa, carbidopa, and benserazide, or an isomer or analog thereof serotonin-norepinephrine reuptake inhibitors (SNRI), such as venlafaxine, desvenlafaxine, duloxetine, levomilnacipran, sibutramine, and milnacipran; tricyclic antidepressants (TCAs), such as amitriptyline, desipramine, doxepin, imipramine, nortriptyline, protriptyline, and trimipramine; 3,4-methylenedioxy-N-methylamphetamine (MDMA); propranolol; and ziprasidone, and risperidone, prazosin, mirtazapine, venlafaxine, lithium, bupropion, trazodone, and carbamazepine, or an isomer or analog thereof. Kits of the invention can optionally include pharmaceutically acceptable carriers and/or diluents. In one embodiment, a kit of the invention includes one or more other components, adjuncts, or adjuvants as described herein. In one embodiment, a kit of the invention includes instructions or packaging materials that describe how to administer and/or how to use a drug or compound or composition of the kit for the treatment of depression, a stress or anxiety disorder, or a neurodegenerative disease or condition. Containers of the kit can be of any suitable material, e.g., glass, plastic, metal, etc., and of any suitable size, shape, or configuration. In one embodiment, a compound or drug, or composition comprising the drug or compound of the invention is provided in the kit as a solid, such as a tablet, pill, chewing gum, or powder form. In another embodiment, a compound or drug, or composition comprising the drug or compound of the invention is provided in the kit as a liquid or solution. In one embodiment, the kit comprises an ampoule or syringe containing a compound or drug, or composition comprising the drug or compound of the invention in liquid or solution form.

To provide for the administration of dosages for the desired therapeutic treatment, in some embodiments, pharmaceutical or physiologically acceptable compositions of the invention can comprise between about 0.1% and 45%, and especially, 1 and 15%, by weight of the total of one or more of the compounds or drugs based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The compounds and drugs of the present invention include all hydrates and salts that can be prepared by those of skill in the art. Under conditions where the compounds and drugs of the present invention are sufficiently basic or acidic to form stable nontoxic acid or base salts, administration of the compounds and drugs as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

It will be appreciated by those skilled in the art that certain of the compounds and drugs of the invention may contain one or more asymmetrically substituted carbon atoms which can give rise to stereoisomers. It is understood that the invention extends to all such stereoisomers, including enantiomers, and diastereoisomers and mixtures, including racemic mixtures thereof.

In vivo application of the subject compounds and drugs, and compositions containing them, can be accomplished by any suitable method and technique presently or prospectively known to those skilled in the art. The subject compounds and drugs can be formulated in a physiologically- or pharmaceutically-acceptable form and administered by any suitable route known in the art including, for example, oral, nasal, rectal, and parenteral routes of administration. As used herein, the term parenteral includes subcutaneous, intradermal, intravenous, intramuscular, intraperitoneal, and intrasternal administration, such as by injection. Administration of the subject compounds and drugs of the invention can be a single administration, or at continuous or distinct intervals as can be readily determined by a person skilled in the art.

The compounds and drugs of the subject invention, and compositions comprising them, can also be administered utilizing liposome technology, slow release capsules, implantable pumps, and biodegradable containers. These delivery methods can, advantageously, provide a uniform dosage over an extended period of time. The compounds and drugs of the invention can also be administered in their salt derivative forms or crystalline forms.

Compounds and drugs of the subject invention can be formulated according to known methods for preparing pharmaceutically and/or physiologically acceptable compositions. Formulations are described in detail in a number of sources which are well known and readily available to those skilled in the art. For example, *Remington's Pharmaceutical*

*Science* by E. W. Martin describes formulations which can be used in connection with the subject invention. In general, the compositions of the subject invention will be formulated such that an effective amount of the compound or drug is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional physiologically-acceptable carriers and diluents which are known to those skilled in the art. Examples of carriers or diluents for use with the subject compounds include ethanol, dimethyl sulfoxide, glycerol, alumina, starch, saline, and equivalent carriers and diluents. To provide for the administration of such dosages for the desired therapeutic treatment, compositions of the invention will advantageously comprise between about 0.1% and 99%, and especially, 1 and 15% by weight of the total of one or more of the subject compounds or drugs based on the weight of the total composition including carrier or diluent.

Compounds and drugs of the invention, and compositions thereof, may be systemically administered, such as intravenously or orally, optionally in combination with a pharmaceutically or physiologically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the active compound or drug may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound or drug may be incorporated into sustained-release preparations and devices.

Compounds or drugs and compositions of the invention, including pharmaceutically acceptable salts or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound or drug of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds and drugs and pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Mammalian species that benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo bison, horses, donkey, swine, sheep, and goats; exotic animals typically found in zoos such as bear, lions, tigers, panthers, elephants, hippopotamus, rhinoceros, giraffes antelopes, sloth, gazelles, zebras, wildebeests, prairie dogs, koala bears, kangaroo opossums, raccoons, pandas, hyena, seals, sea lions, elephant seals, otters, porpoises dolphins, and whales. As used herein, the terms "subject" "host", and "patient" are used interchangeably and intended to include such human and non-human mammalian species.

Neurodegenerative diseases and conditions contemplated within the scope of the invention include, but are not limited to, Alzheimer's disease, Parkinson's disease, Huntington's disease, amyotrophic lateral sclerosis (ALS), stroke, spinal cord injury, gangliogliomas and gangliocytomas, argyrophilic grain dementia, corticobasal degeneration, dementia pugilistica, frontotemporal dementia with parkinsonism linked to chromosome17, Pick's disease, Hallervorden-Spatz disease, myotonic dystrophy, Niemann-Pick disease (type C), Parkinsonism-dementia complex of Guam, postencephalitic parkinsonism, prion diseases (some), progressive subcortical gliosis, and progressive supranuclear palsy.

Methods of the invention can be used in conjunction with other drugs for the treatment of depression, anxiety or stress disorders, and/or neurodegenerative conditions, including, for example, donepezil, galantamine, vivastigmine, memantine, rivastigmine, or selegiline; monoamine oxidase (MAO) inhibitors such as phenelzine, tranylcypromine, isocarboxazid, and selegiline; antiepileptic drugs; selective serotonin reuptake inhibitors (SSRI), such as citalopram, escitalopram, fluvoxamine, fluoxetine, vortioxetine, paroxetine, sertraline, rasagiline, selegiline, L-dopa, carbidopa, and benserazide, or an isomer or analog thereof; serotoninnorepinephrine reuptake inhibitors (SNRI), such as venlafaxine, desvenlafaxine, duloxetine, levomilnacipran, sibutramine, and milnacipran; tricyclic antidepressants (TCAs), such as amitriptyline, desipramine, doxepin, imipramine, nortriptyline, protriptyline, and trimipramine; 3,4-methylenedioxy-N-methylamphetamine (MDMA); propranolol; and ziprasidone, and risperidone, prazosin, mirtazapine, venlafaxine, lithium, bupropion, trazodone, and carbamazepine, or an isomer or analog thereof. Methods of the invention can also be used in combination with other therapies for stress disorders, including, for example, various forms of psychotherapy, yoga, and the like.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 4,938,949
Sinars, C., J. Cheung-Flynn, R. Rimerman, J. Scammell, D. Smith, J. Clardy "Structure of the large FK506-binding protein FKBP51, an Hsp90-binding protein and a component of steroid receptor complexes" *PNAS,* 2003, 100 (3):868-873.
Stechschulte, L. et al. "FKBP51 Reciprocally Regulates GRα and PPARγ Activation via the Akt-p38 Pathway" *Mol. Endocrinol.,* 2014, 28(8):1254-1264.

We claim:

1. A method for treating a neurodegenerative disease or condition, or depression, a stress disorder, and/or an anxiety disorder in a person or animal having said neurodegenerative disease or condition, or depression, a stress disorder, and/or an anxiety disorder, the method comprising administering to the person or animal a therapeutically effective amount of one or more compounds or drugs, or a composition comprising said one or more compounds or drugs, that inhibits FKBP51 activity or function, wherein the person or animal exhibits one or more single nucleotide polymorphisms (SNPs) in the FKBP5 gene, and wherein said one or more SNPs are associated with elevated levels of FKBP51 protein.

2. The method according to claim 1, wherein the person or animal exhibits increased levels of FKBP51 protein relative to a control.

3. The method according to claim 1, wherein the compound or drug is one that lessens or attenuates the suppressive effect of FKBP51 on glucocorticoid receptor (GR) activity.

4. The method according to claim 1, wherein said compound or drug is provided in the form of a pharmaceutically or physiologically acceptable salt.

5. The method according to claim 1, wherein the method further comprises a step of determining whether the person or animal exhibits elevated levels of FKBP51 protein.

6. The method according to claim 1, wherein the stress disorder is a post-traumatic stress disorder (PTSD).

7. The method according to claim 1, wherein the neurodegenerative disease is Alzheimer's disease.

8. The method according to claim 1, wherein the method further comprises treating the person or animal with one or more drugs or compounds approved for treating a neurodegenerative disease, or for treating depression, a stress disorder, or an anxiety disorder.

9. The method according to claim 8, wherein said approved drug or compound is one or more of donepezil, galantamine, vivastigmine, memantine, rivastigmine, or selegiline; or one or more of monoamine oxidase (MAO) inhibitors; antiepileptic drugs; selective serotonin reuptake inhibitors (SSRI); serotonin-norepinephrine reuptake inhibitors (SNRI); tricyclic antidepressants (TCAs); 3,4-methylenedioxy-N-methylamphetamine (MDMA); propranolol; or ziprasidone, or risperidone, prazosin, mirtazapine, venlafaxine, lithium, bupropion, trazodone, or carbamazepine.

10. The method according to claim 1, wherein the method further comprises a step of determining whether the person or animal exhibits one or more SNPs that are associated with elevated levels of FKBP51 protein.

11. The method according to claim 1, wherein the compound or drug is benztropine, clonidine, pimozide, thioridazine, trifluoperazine, or triflupromazine, or a pharmaceutically or physiologically acceptable salt thereof.

12. The method according to claim 1, wherein the compound or drug is benztropine mesylate, clonidine hydrochloride, thioridazine hydrochloride, trifluoperazine dihydrochloride, or triflupromazine hydrochloride.

13. The method according to claim 9, wherein said one or more monoamine oxidase (MAO) inhibitors is phenelzine, tranylcypromine, isocarboxazid, or selegiline.

14. The method according to claim 9, wherein said one or more selective serotonin reuptake inhibitors (SSRI) is citalopram, escitalopram, fluvoxamine, fluoxetine, vortioxetine, paroxetine, sertraline, rasagiline, selegiline, L-dopa, carbidopa, or benserazide.

15. The method according to claim 9, wherein said one or more serotonin-norepinephrine reuptake inhibitors (SNRI) is venlafaxine, desvenlafaxine, duloxetine, levomilnacipran, sibutramine, or milnacipran.

16. The method according to claim 9, wherein said one or more tricyclic antidepressants (TCAs) is amitriptyline, desipramine, doxepin, imipramine, nortriptyline, protriptyline, or trimipramine.

* * * * *